United States Patent
Radojicic

(10) Patent No.: US 9,770,180 B2
(45) Date of Patent: Sep. 26, 2017

(54) SYSTEM AND METHOD FOR MONITORING AND DELIVERING THERAPEUTICS TO THE SPINAL CORD

(76) Inventor: Milan Radojicic, Los Gatos, CA (US)

(\*) Notice: Subject to any disclaimer, the term of this patent is extended or adjusted under 35 U.S.C. 154(b) by 1430 days.

(21) Appl. No.: 12/228,697

(22) Filed: Aug. 16, 2008

(65) Prior Publication Data

US 2009/0227851 A1   Sep. 10, 2009

Related U.S. Application Data

(63) Continuation-in-part of application No. 11/840,213, filed on Aug. 16, 2007, now abandoned.

(60) Provisional application No. 60/822,640, filed on Aug. 17, 2006.

(51) Int. Cl.
   A61B 5/03   (2006.01)
   A61M 25/00  (2006.01)
   A61M 5/172  (2006.01)

(52) U.S. Cl.
   CPC ........... *A61B 5/032* (2013.01); *A61M 5/1723* (2013.01); *A61M 25/00* (2013.01); *A61M 2005/1726* (2013.01); *A61M 2025/0002* (2013.01); *A61M 2025/0003* (2013.01); *A61M 2025/0057* (2013.01); *A61M 2210/1003* (2013.01)

(58) Field of Classification Search
   CPC .......... A61B 5/032; A61M 2005/1726; A61M 2025/0057; A61M 2210/1003; A61M 25/00; A61M 5/1723; A61M 2025/0001; A61M 2025/0002; A61M 2025/003
   USPC ............... 604/500, 506, 93.01; 600/433, 309
   See application file for complete search history.

(56) References Cited

U.S. PATENT DOCUMENTS

| | | |
|---|---|---|
| 4,583,968 A | 4/1986 | Mahurkar |
| 4,904,237 A | 2/1990 | Janese |
| 5,221,256 A | 6/1993 | Mahurkar |
| 5,325,865 A | 7/1994 | Beckman et al. |
| 5,378,230 A | 1/1995 | Mahurkar |
| 5,686,289 A | 11/1997 | Humes et al. |
| 5,827,237 A | 10/1998 | Macoviak et al. |
| 6,626,902 B1 * | 9/2003 | Kucharczyk et al. ......... 606/41 |
| 7,150,737 B2 | 12/2006 | Purdy et al. |
| 2002/0082556 A1 * | 6/2002 | Cioanta et al. ............... 604/113 |
| 2003/0097082 A1 * | 5/2003 | Purdy et al. .................. 600/594 |
| 2004/0087863 A1 * | 5/2004 | Eide .............................. 600/500 |

(Continued)

OTHER PUBLICATIONS

Modern Marvels Invent Now Challenge, Certificate of Recognition, 2006, 2 pages.

(Continued)

*Primary Examiner* — Kevin C Sirmons
*Assistant Examiner* — William Carpenter

(57) ABSTRACT

This invention is a continuous monitor of the spinal cord and brain microenvironment in injury and disease that also allows therapeutic interventions. It utilizes a multiport catheter that contains a transducer at the tip for monitoring spinal physiological parameters and also allows via additional ports for sampling and exchange of spinal fluid, as well as drug delivery to the central nervous system. This invention allows for more precise therapeutic interventions in spinal cord and brain injury and disease. If the pressure monitor is mounted to the patient, the wireless data transmitter may also send a wireless signal to a wireless data receiver for display on a wireless data display. The catheter would allow for wireless transmission of physiological parameters.

2 Claims, 4 Drawing Sheets

(56) References Cited

U.S. PATENT DOCUMENTS

| | | |
|---|---|---|
| 2004/0193045 A1* | 9/2004 | Scarborough et al. ....... 600/432 |
| 2005/0020962 A1* | 1/2005 | Reich et al. ....................... 604/8 |
| 2005/0171452 A1* | 8/2005 | Neff ............................. 600/549 |
| 2006/0047201 A1* | 3/2006 | Eide .............................. 600/485 |
| 2007/0179427 A1 | 8/2007 | Radojicic |
| 2009/0227025 A1 | 9/2009 | Nichols et al. |
| 2011/0004304 A1 | 1/2011 | Tao et al. |
| 2011/0060265 A1 | 3/2011 | Dragoon et al. |

OTHER PUBLICATIONS

Bateman, Grant A., "The Role of Altered Impedance in the Pathophysiology of Normal Pressure Hydrocephalus, Alzheimer's Disease and Syringomyelia", Medical Hypothesis 63, Apr. 2004, pp. 980-985.

Aygok, Gunes A., et al., "Cerebrospinal Fluid Infusion Studies: Current View and Concepts in Assessment of Post-Traumatic Hydrocephalus", International Brain Injury Association, Issue 04 2010, 3 pages.

El Sankari et al., "Cerebrospinal Fluid and Blood Flow in Mild Cognitive Impairment and Alzheimer's Disease: A Differential Diagnosis from Idiopathic Normal Pressure Hydrocephalus", BioMed Central, Fluids and Barriers of the CNS, 2011, 11 pages.

Johanson, Conrad, et al., "Periventricular Destabilization and Ventriculomegaly in Aging Rats: Implications for Reduced Neurogenesis and Cognition", SRHSB, http://www.srhsb.org/, 2009, 3 pages.

Radojicic, Milan, et al., "Ascending Central Canal Dilation and Progressive Ependymal Disruption in a Contusion Model of Rodent Chronic Spinal Cord Injury", BMC Neurology 7, No. 1, 2007: 30, 12 pages.

ISA/KR, PCT International Search Report and Written Opinion, Application No. PCT/US2012/070415, dated Apr. 10, 2013, 11 pages.

Aygok, Gunes A., et al., "Cerebrospinal Fluid Infusion Studies: Current View and Concepts in Assessment of Post-Traumatic Hydrocephalus", International Neurotrauma Letter, Issue 22, International Brain Injury Association, http://www.internationalbrain.org/enews/ntl-issue-22/ 2010, 3 pages.

Bell, Rodney D., et al., "Ventriculo-Lumbar Perfusion in Acute Ischemic Stroke" Neurocritical Care, 2006; vol. 5, pp. 21-29.

Marmarou, Anthony, et al., "A Nonlinear Analysis of the Cerebrospinal Fluid System and Intracranial Pressure Dynamics", J. Neurosurg., vol. 48, Mar. 1978, pp. 332-344.

* cited by examiner

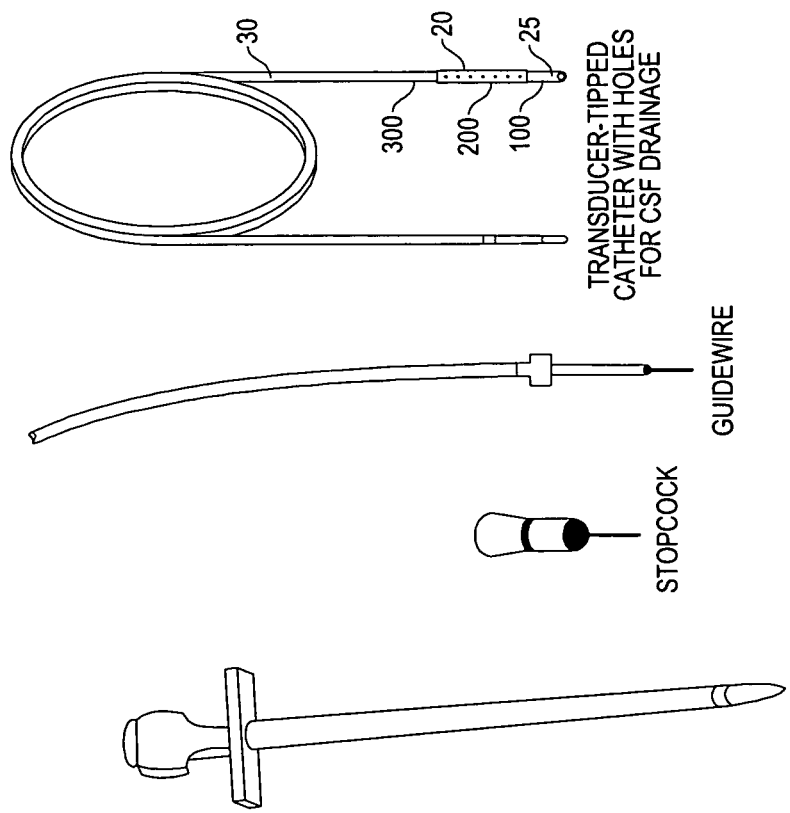
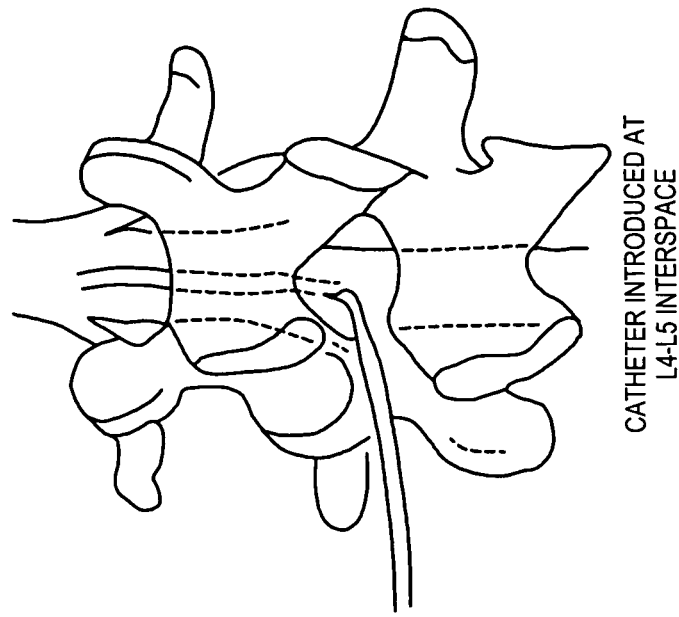

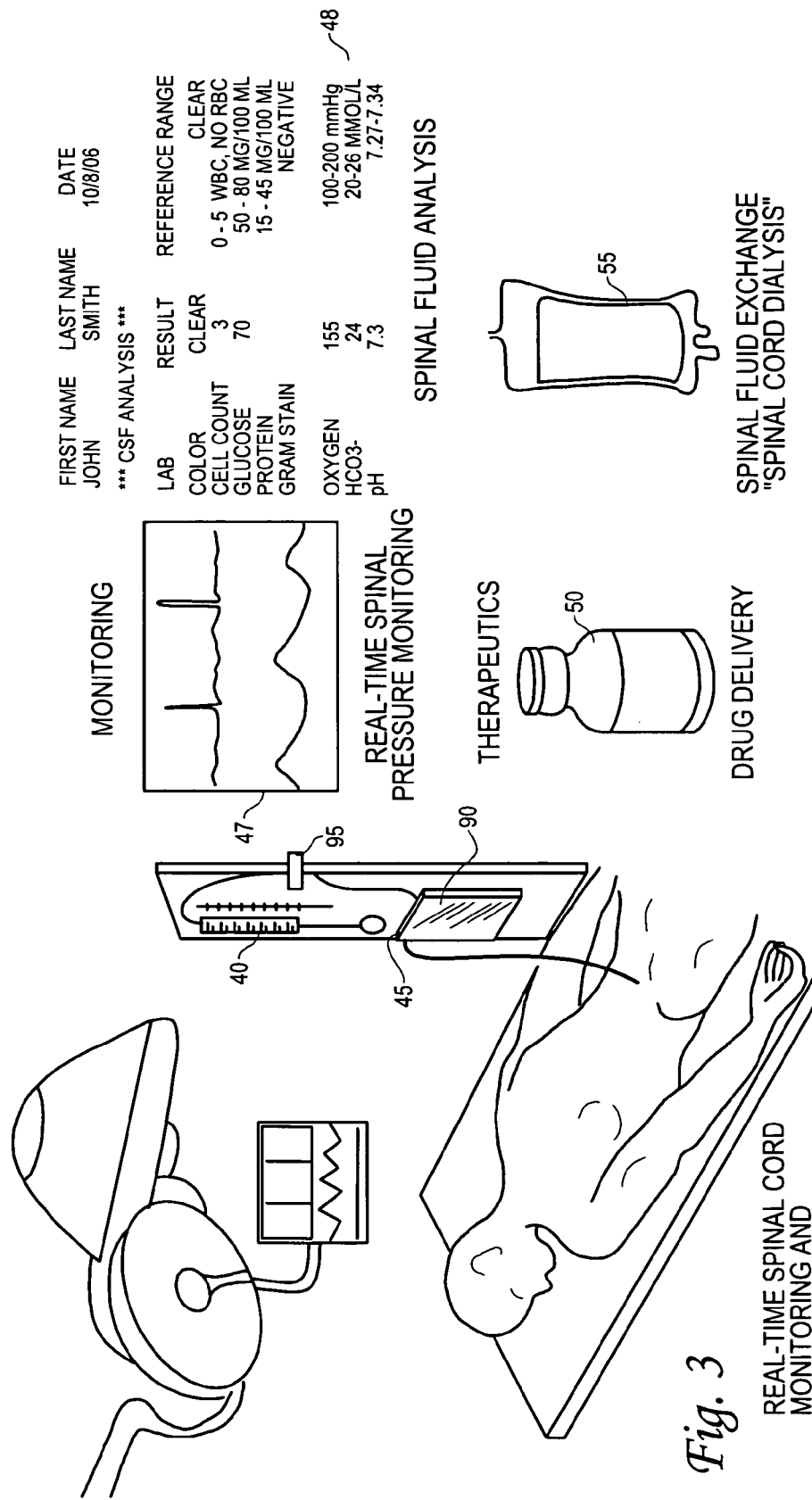

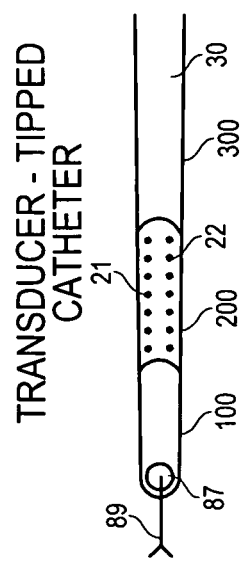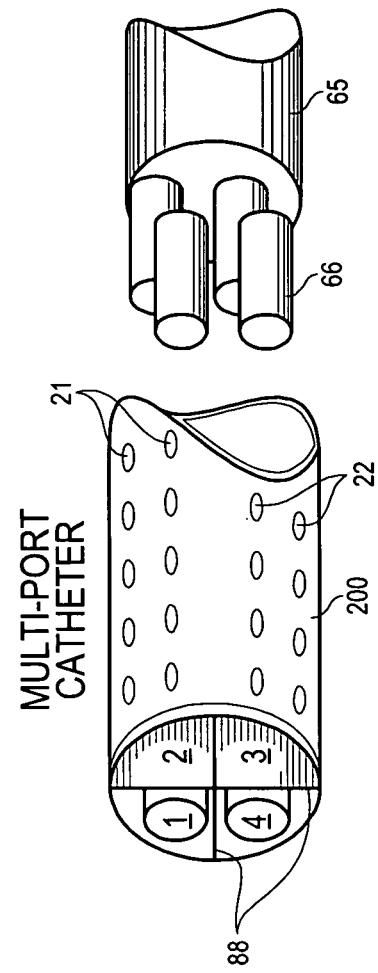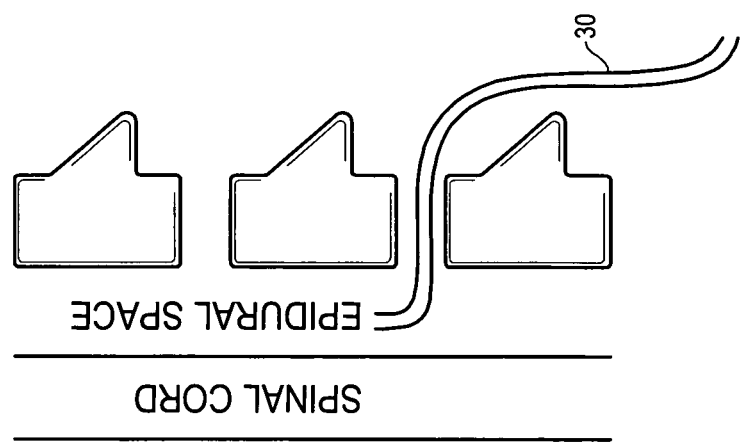

SYSTEM AND METHOD FOR MONITORING AND DELIVERING THERAPEUTICS TO THE SPINAL CORD

This continuation-in-part application claims priority from co-pending nonprovisional application Ser. No. 11/840,213 filed Aug. 16, 2007 now abandoned by the same inventor Milan Radojicic which in turn claims priority from provisional application Ser. No. 60/822,640 filed Aug. 17, 2006.

DISCUSSION OF RELATED ART

The present invention relates generally to surgical methods and medical devices. More particularly, it concerns methods and devices for monitoring and delivering therapeutics to the spinal cord and brain along a spinal fluid pathway or cistern, particularly the lumbar cistern.

By the end of the next decade, 300,000 people will be living with chronic spinal cord injury in the US alone. Advances in medical and rehabilitative care have improved survival rates for these individuals, but many experience clinical decline even years after the initial injury. Clinical decline is often accompanied by a slow and progressive cavitation of the central spinal cord, known as post-traumatic syringomyelia. The pathogenesis of this disease remains poorly understood, but may be related to spinal cord edema and altered intraspinal pressure due changes in spinal fluid homeostasis. Beyond spinal cord injury, other spinal cord diseases may similarly be impacted by such pathophysiological processes. Such diseases include spinal tumors and vascular malformations, spinal infections, multiple sclerosis, transverse myelitis, and non-traumatic syringomyelia. Moreover, considerable morbidity and mortality may result from spinal surgical interventions where monitoring has been heretofore limited to the electrophysiological parameters.

Following spinal cord injury and disease, normal CSF dynamics may be distorted by a number of possible mechanisms, including subarachnoid CSF outflow obstructions, changes in compliance of the subarachnoid space, or elevated intraspinal pressures. Altered CSF dynamics are believed to result in localized spinal cord edema, known as the presyrinx state that subsequently gives rise to central canal dilation and/or the formation of intraspinal glial-lined parenchymal cysts.

The propagation of intraspinal cavities requires a driving force sufficient to propel fluid via a one-way valve mechanism into the cysts, which often contain fluid at a higher pressure than the subarachnoid space. Proposed driving forces include cardiac pulsations along vessels, postural changes and valsalva movements and elevated intraspinal pressures. Perhaps, transient hypertensive episodes of autonomic dysreflexia is a potential driving force.

The measurement and treatment of raised intracranial pressures following insults to the brain is very well established and is based on many years of work in experimental neurology establishing a pressure-volume relationship in cranial compartment, first suggested by Alexander Monro in 1783. With the increasing recognition on the role of spinal edema, pressure and altered cerebrospinal fluid dynamics on spinal cord injury and disease, there has been a long felt need in the industry for monitoring such phenomena. Indeed, continuous monitoring of various physiological parameters is a mainstay of modern critical care. Prior art has focused on intracranial pressure monitoring, for example see Beckman et al. U.S. Pat. No. 5,325,865. Purdy et al. 7,150,737 B2 would allow for navigating the subarachnoid space, but limit interventions to heating and cooling of the nervous tissue. Thus, an object of the invention is to provide continuous monitoring of several spinal physiological parameters, along with a method of drug delivery and therapeutics.

A variety of catheter structures have been created for cycling fluid, such as Mahurkar in U.S. Pat. No. 4,583,968 issued Apr. 22, 1986 the disclosure of which is incorporated herein by reference. The Mahurkar catheter provides an elongated cylindrical tube for injection and removal of fluid. Unfortunately, the Mahurkar catheter provides an uncomfortable configuration for user. Another dual lumen catheter is discussed by Macoviak in U.S. Pat. No. 5,827,237 issued Oct. 27, 1998, the disclosure of which is incorporated herein by reference. The Macoviak catheter is specially shaped and specialized for heart surgery.

SUMMARY OF THE INVENTION

The present invention involves introducing a catheter in an interspace of the spine. FIG. 1 shows typical parts needed for insertion of a catheter. A scoop shaped toughey needle which is a large gauge needle is first inserted into the interspace with the elongated oval tip opening facing upward. A guide wire is inserted through the toughey needle and gently placed in the epidural space. The guide wire guides a transducer tipped catheter into the epidural space through the interspace. A stopcock plugs the catheter during insertion. After the catheter is introduced, the guide wire and needle are both removed. FIG. 2 shows the catheter introduced. After the catheter is introduced, the patient lays down as seen in FIG. 3. While the patient is laying down, the transducer provides monitoring of pressure and spinal fluid. Optionally, spinal fluid can be exchanged in a spinal cord dialysis. Also, therapeutics and drug delivery can be introduced via the catheter. Drug delivery can be pain medicine or anti-inflammatory medicine, or any other type of medicine. Pain medicine is desirable since having a catheter inserted in epidural space between spinal cord and bones is typically not very comfortable, see FIG. 5.

BRIEF DESCRIPTION OF THE DRAWINGS

FIG. 1 is a diagram of standard equipment necessary for introducing a catheter.

FIG. 2 is a diagram of a catheter introduced the L4-L5 interspace.

FIG. 3 is a diagram of a patient laying on a table with real-time spinal cord monitoring and therapeutics.

FIG. 4 is a diagram showing pressure monitoring, spinal fluid analysis monitoring, drug delivery and spinal fluid exchange options available after insertion of the catheter.

FIG. 5 is a diagram showing catheter introduction into the epidural space between spinal cord and bones.

FIG. 6 is a diagram of a transducer tipped catheter.

FIG. 7 is a diagram of a four section transducer tipped catheter.

Figure 8:
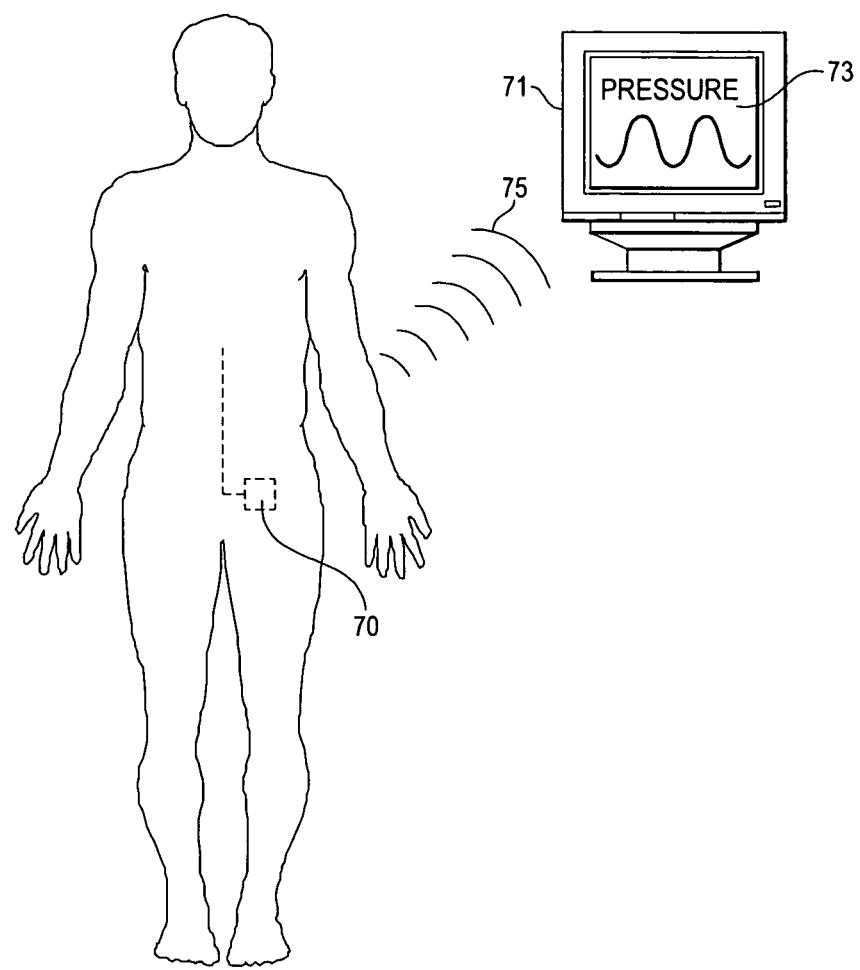
FIG. 8 is a diagram of a wireless embodiment.

The following call a list of elements is consistently used throughout the drawings.

1 First Chamber
2 Second Chamber
3 Third Chamber
4 Fourth Chamber
20 Fluid Apertures
25 Transducer
30 Catheter
40 Pressure Monitor 45 Fluid Pump
47 Pressure Status Display
48 Spinal Fluid Analysis Data
50 Medication
55 Spinal Fluid Exchange Apparatus
70 Wireless Data Transmitter
71 Wireless Data Receiver
73 Wireless Data Display
75 Wireless Signal
88 Axial Segmentation Dividing Panels
90 Spinal Fluid Exchange Device
95 Dialyzer

DETAILED DESCRIPTION OF THE INVENTION

This invention allows a continuous monitoring of the spinal cord and brain microenvironment for injury and disease that also allows therapeutic interventions. The device utilizes a multiport catheter that contains a transducer at the tip for monitoring spinal physiological parameters and also allows via additional ports for sampling and exchange of spinal fluid, as well as drug delivery to the central nervous system. This invention allows for more precise therapeutic interventions in spinal cord and brain injury and disease.

A catheter 30 typically has a circular cross-section and in this case can include a transducer tip 25. The catheter 30, FIG. 7 is segmented into preferably four separate chambers 1, 2, 3, 4 that have openings on an external periphery. The segmentation when seen in cross-section provides a first chamber 1, a second chamber 2 to the right of the first chamber, a third chamber 3 below the second chamber, and a fourth chamber 4 to the left of the third chamber. Each of the chambers are formed by axial segmentation dividing panels 88 formed within the multiport catheter. The panel configuration could be linear, or radial or axial. The panels are connected to the catheter and are preferably formed of the same type of material, such as soft silicone that will not hurt too much when stuck into a person's back. The multiport catheter shown therefore has two pairs of an equal sized arc shaped segmented body that connects to two pairs of tubing. The catheter 30, FIG. 7 has the second and third chambers 2, 3 dedicated to flow of spinal fluid. The spinal fluid may flow in either direction. The second chamber may allow fluid to enter and to the third chamber may allow the fluid to exit. Alternatively, the second chamber may allow the fluid to exit and the third chamber may allow the fluid to exit. The plurality of apertures on the second chamber can be round or oval-shaped as shown in the drawing. The apertures are preferably arranged in rows. The first chamber may also have a plurality of apertures for receiving spinal fluid. Alternatively, the first chamber may be used to feed an electrical wire to a pressure sensor in the tip of the catheter.

Additionally, a fluid pump 45 can circulate spinal fluid. The fluid pump 45 can be automatically deactivated when measuring pressure at a pressure monitor 40. Pressure monitoring provides a real-time pressure status display 47. Additionally, spinal fluid analysis data 48 can also be displayed on the status display 47. Additionally, medication 50 can be delivered through the fluid pump 45 driving medication through the catheter. Additionally, spinal fluid exchange may incorporate a spinal fluid exchange apparatus allowing spinal cord dialysis.

Sometimes, not all the lumens need to be of the same structure. For example, the multiple lumen catheter with an elongated cylindrical tube having an internal diametral septum extending along the length thereof can form a pair of major lumens having semicircular transverse cross-sections with a small third lumen. Mahurkar in U.S. Pat. No. 5,221,256 provides a method for making three lumens with two of them larger and one of them smaller, the disclosure of which is incorporated herein by reference. The present invention may use the Mahurkar multiple lumen structure with the smaller third lumen hooked up to electrical wire, while the two larger lumens transport liquid. The tube connection to the multiple port catheter provides a variety of options for the physician. Alternatively, if the third lumen is for a surgical tool pathway that is too big for the small lumen configuration, the multiple lumen catheter could be made in the configuration of Mahurkar's crescent shaped configuration as shown in U.S. Pat. No. 5,378,230 issued Jan. 3, 1995, the disclosure of which is incorporated herein by reference. The Mahurkar's crescent shaped configuration makes the in and out lumens smaller and the third lumen bigger. In any case, there are a wide variety of geometric configurations commonly and commercially available for configuring the lumens. The best mode is to have the lumens of the catheter configured as four axially symmetrical pie shaped quadrants oriented 90° to each other.

The second step is to insert a transducer tipped catheter in an interspace of the spine, but the first step is to select and configure the transducer. The catheter, FIG. 6 is a multi-port catheter with holes or apertures for CSF outflow and inflow, pressure monitoring and an additional unused port. The configuration of the transducer allows a variety of tools to be introduced through the multiport catheter. Each port terminates at a chamber of the transducer mounted at the tip of the catheter. In the four chamber embodiment, the first pair of chambers can be used for cycling spinal fluid. The second pair of chambers can be used for pressure monitoring, pressure sensor mounting or for introducing surgical instruments into the interspace of the spine, such as a camera for viewing the inside of the interspace of the spine, or for any other surgical instrument such as a metal cutting tool or laser.

The transducer uses a single port which is called the transducer port. The transducer can be activated and active while a spinal fluid exchange device 90 exchanges spinal fluid. The spinal fluid exchange device 90 can handle cerebrospinal fluid so that it is drained and exchanged with an inflow of artificial cerebrospinal fluid. A dialyzer 95 can drain cerebrospinal fluid, treat (e.g., dialyzed of a substance) and re-circulate into the subarachnoid space.

If the pressure monitor is mounted to the patient, FIG. 8, the wireless data transmitter 70 may also a wireless signal 75 to a wireless data receiver 71 for display on a wireless data display 73.

In some embodiments, the multi-chambered/port catheter that would house additional sensors not limited to pressure, pH, temperature, oxygenation/CO2/other gases, systolic/diastolic variations in CSF pulsation, electrolytes, metabolite concentrations, glucose, protein, cell count, gram stain and culture, etc. Ports would allow for sampling, removal and exchange of spinal fluid thereby allowing infusion studies to establish a pressure/volume relationship of the spinal compartment and compliance/impedance measurements of the spinal cord in injury and disease, as well as "spinal cord dialysis" and drug delivery. Measurements would occur at baseline and after physiologic maneuvers, such as a valsalva or a Queckenstedt test, and would be compared to standard values established with normal control subjects. Monitoring would occur continuously or intermittently, in the acute, subacute or chronic phase of injury and disease of the spinal cord. These measurements would allow for more precise therapeutic interventions. The catheter's I/O system could be attached directly to an external monitor and reservoir via a wire and tubing or have an internal (subcutaneous) or external portable unit/reservoir/pump with transmitter which sends a wireless signal to an external receiver and data processor. The I/O data could be used to automate delivery of therapeutics based on the current state of the patient, in order to achieve homeostasis.

Ultrasonic waves could be applied or near a spinal cord injury or disease segment at the posterior and anterior subarachnoid spaces at the lesion or or at a cistern (e.g., but not limited to the lumbar cistern at pr just below the conus medullaris and at the L5/S1 dural sac) to document cerebrospinal fluid pulsation of the cauda equina. Among the measurements, oscillation rate and amplitude could be measured in disease and injury and compared to established standards based on normal control subjects.

Microtools, as described above, may include any of, but is not limited to scissors, scalpel, laser, electrothermy, suturing tools.

Additionally, another method and invention consists of the intrathecal administration and exchange of a preferably hyperosmolar or alternatively hypotonic artificial CSF solution for the purpose of flushing toxic metabolites, inflammatory cells and proteins and blood from the injured or disease spinal cord via a specialized intrathecal catheter. This treatment can be conducted in the acute, subacute or chronic phase.

Another method and invention is the introduction of a multi-port catheter into the epidural or subarachnoid space that would allow drug delivery or introduction of a camera and/or precise micro-tools for the ablation of any dural scarring and dural repair.

While the above description contains many specificities, these should not be construed as limitations on the scope of the invention, but as exemplifications of the presently preferred embodiments thereof. Many other ramifications and variations are possible within the teaching of the invention. Additionally, any combination of the above examples may be possible. Thus the scope of the invention should be determined by the appended claims and their legal equivalents, rather than the examples given.

The invention claimed is:

1. A spinal catheter comprising:
an elongate shaft having a distal end and a proximal end, wherein the distal end is adapted for placement in a spinal fluid pathway, epidural space, ventricle or cistern;
monitoring lumen connected to a monitoring port at a distal end, wherein the monitoring port is a first port housing a transducer, wherein the transducer determines pressure data in the spinal fluid pathway, epidural space, ventricle or cistern;
an inlet lumen formed on the elongate shaft and connected to an inlet port, wherein the inlet port is a second port;
an outlet lumen connected to an outlet port, wherein the outlet port is a third port, wherein at least one of the inlet port and the outlet port supplies infuses or exchanges fluid to establish changes in volume;
an I/O system configured to receive the pressure data and generate impedance measurements based upon the relationship between the changes in volume and the pressure data;
wherein the transducer can transmit and collect electromagnetic radiation, in at least one of the ultrasonic, infrared range, and visible range; and
wherein the transducer continuously monitors structural data of the spinal cord, including central canal size and parenchymal edema.

2. A spinal catheter comprising:
an elongate shaft having a distal end and a proximal end, wherein the distal end is adapted for placement in a spinal fluid pathway, epidural space, ventricle or cistern;
monitoring lumen connected to a monitoring port at a distal end, wherein the monitoring port is a first port housing a transducer, wherein the transducer determines pressure data in the spinal fluid pathway, epidural space, ventricle or cistern;
an inlet lumen formed on the elongate shaft and connected to an inlet port, wherein the inlet port is a second port;
an outlet lumen connected to an outlet port, wherein the outlet port is a third port, wherein at least one of the inlet port and the outlet port supplies infuses or exchanges fluid to establish changes in volume;
an I/O system configured to receive the pressure data and generate impedance measurements based upon the relationship between the changes in volume and the pressure data;
wherein the catheter has at least four ports total: wherein a fourth port is a surgical tool port and receives a surgical tool, further comprising a transducer mounted to the monitoring port, wherein the transducer forms the distal end of the spinal catheter;
wherein the transducer can transmit and collect electromagnetic radiation, in at least one of the ultrasonic, infrared range, and visible range; and
wherein the transducer continuously monitors structural data of the spinal cord, including central canal size and parenchymal edema, wherein the transducer continuously monitors flow characteristics of the spinal cord, including blood and cerebrospinal fluid velocity, wherein the transducer is a pressure sensor, wherein the transducer monitors spinal fluid pressure, wherein the transducer monitors cerebrospinal compliance.

* * * * *